US011000736B2

(12) United States Patent
Luzzatto (10) Patent No.: US 11,000,736 B2
(45) Date of Patent: May 11, 2021

(54) METHOD AND APPARATUS FOR AN ACTIVITY ENVIRONMENT GENERATOR

(71) Applicant: Yuval Luzzatto, Tel Aviv (IL)

(72) Inventor: Yuval Luzzatto, Tel Aviv (IL)

(*) Notice: Subject to any disclaimer, the term of this patent is extended or adjusted under 35 U.S.C. 154(b) by 0 days.

(21) Appl. No.: 16/756,436

(22) PCT Filed: Oct. 11, 2018

(86) PCT No.: PCT/IL2018/051099
§ 371 (c)(1),
(2) Date: Apr. 15, 2020

(87) PCT Pub. No.: WO2019/073473
PCT Pub. Date: Apr. 18, 2019

(65) Prior Publication Data
US 2020/0276476 A1 Sep. 3, 2020

(30) Foreign Application Priority Data
Oct. 15, 2017 (IL) .......................................... 255036

(51) Int. Cl.
*A63B 24/00* (2006.01)
*A63B 21/005* (2006.01)
(Continued)

(52) U.S. Cl.
CPC ........ *A63B 24/0087* (2013.01); *A63B 21/005* (2013.01); *A63B 21/008* (2013.01);
(Continued)

(58) Field of Classification Search
CPC ..... G06F 3/014; G06F 3/012; G06K 9/00355; G16H 20/30; A63B 24/0087;
(Continued)

(56) References Cited

U.S. PATENT DOCUMENTS 8,968,220 B2 * 3/2015 Han ................. A63B 23/03508
601/5
9,005,145 B2 * 4/2015 Champsaur ........ A63B 24/0006
601/5
(Continued)

FOREIGN PATENT DOCUMENTS

WO    WO 1995/01769 A2    1/1995
WO    WO 2006/102529 A2    9/2006
(Continued)

OTHER PUBLICATIONS

International Searching Authority, International Search Report and Written Opinion for Application No. PCT/IL2018/051099, dated Feb. 3, 2019, 15 pages, The Israel Patent Office, Israel.
(Continued)

*Primary Examiner* — Sundhara M Ganesan
(74) *Attorney, Agent, or Firm* — Alston & Bird LLP (57) ABSTRACT

A method and apparatus for Activity Environment Generator ("AEG") is provided. The AEG allows a user in a variety of settings such as: domestic settings, office chairs, TV chairs, train seats, airplane seats, domestic or hospital beds. The AEG is particularly useful in the fields of rehabilitation, physiotherapy, injury prevention, falls prevention, training and wellness in general and may also provide recreational and/or entertainment elements. The AEG provides dynamically controllable forces with which the user interacts in the course of his/her activity. In one aspect of the invention, the forces provided by the AEG are generated by a magnetic field. In another aspect of the invention, the forces provided by The AEG are generated by a pneumatic actuator. The AEG is optionally scalable and/or modular and, in specific embodiments, may include one or more of the following: a Remote Trainer, an AEG-Accessory, an AEG-Wearable, optimization by Big Data and machine-learning.

46 Claims, 8 Drawing Sheets

(51) Int. Cl.
    A63B 21/008    (2006.01)
    G06K 9/00      (2006.01)
    G06F 3/01      (2006.01)
    G16H 20/30     (2018.01)

(52) U.S. Cl.
    CPC .............. G06F 3/012 (2013.01); G06F 3/014 (2013.01); G06K 9/00355 (2013.01); G16H 20/30 (2018.01); *A63B 24/0062* (2013.01); *A63B 2024/0093* (2013.01)

(58) Field of Classification Search
    CPC .......... A63B 21/008; A63B 2024/0093; A63B 21/005; A63B 24/0062
    See application file for complete search history.

(56) References Cited

U.S. PATENT DOCUMENTS

| | | | | |
|---|---|---|---|---|
| 2002/0022550 | A1* | 2/2002 | Pham | A63B 21/4001 482/1 |
| 2008/0132383 | A1* | 6/2008 | Einav | A61H 3/008 482/8 |
| 2009/0023122 | A1* | 1/2009 | Lieberman | A61H 23/0245 434/258 |
| 2012/0058861 | A1* | 3/2012 | Satut | A63B 6/00 482/8 |
| 2014/0135960 | A1* | 5/2014 | Choi | G09B 19/0038 700/91 |
| 2014/0277739 | A1* | 9/2014 | Kornbluh | A41D 13/002 700/260 |
| 2015/0173993 | A1* | 6/2015 | Walsh | B25J 9/0006 414/4 |
| 2015/0297934 | A1* | 10/2015 | Agrawal | A63B 21/4025 482/4 |
| 2016/0121166 | A1* | 5/2016 | Oshima | A63B 21/4033 482/4 |
| 2017/0246506 | A1* | 8/2017 | Waldman | A63B 21/0058 |
| 2017/0361165 | A1* | 12/2017 | Miller | A63B 24/0006 |
| 2018/0104542 | A1* | 4/2018 | Kwon | A63B 22/04 |
| 2018/0345066 | A1* | 12/2018 | Bertrand | A63B 21/4033 |

FOREIGN PATENT DOCUMENTS

| | | |
|---|---|---|
| WO | WO 2008/002644 A2 | 1/2008 |
| WO | WO 2014/140422 A1 | 9/2014 |
| WO | WO 2016/154271 A1 | 9/2016 |

OTHER PUBLICATIONS

International Preliminary Examining Authority, International Preliminary Report on Patentability for Application No. PCT/IL2018/051099, dated Feb. 20, 2020, 26 pages, The Israel Patent Office, Israel.

* cited by examiner

METHOD AND APPARATUS FOR AN ACTIVITY ENVIRONMENT GENERATOR

CROSS-REFERENCE TO RELATED APPLICATIONS

This application is a national stage entry of International Patent Application No. PCT/IL2018/051099, filed on Oct. 11, 2018, which claims priority to and the benefit of Israel Application No. 255036, filed on Oct. 15, 2017, each of which is incorporated herein by reference in its entirety.

FIELD OF THE INVENTION

The invention relates to a method and apparatus for the generation of an activity environment, particularly useful in the framework of low-impact exercise of specific areas and, in particular, in the field of rehabilitation, physiotherapy, injury prevention, falls prevention training and wellness in general.

The invention may also make use of recreational and/or entertainment elements for purpose of improving the user's experience and results in the course of the activity.

BACKGROUND OF THE INVENTION

The aim of the invention disclosed in this application is to provide an Activity Environment Generator ("AEG") apparatus and method that allow a user ("User") to create an Activity Environment and interact with the same, in a setting which is not, usually, designed and/or equipped for such Activity. Examples of typical settings include: domestic settings, office chairs, TV chairs, train seats, domestic or hospital beds and so forth.

The invention is particularly useful for exercises directed to the prevention of injuries caused by accidents such as falls of elderly people.

More generically, the invention is useful for the slowing down of physical decline due to aging, for persons of all ages who need rehabilitation following an injury, an illness or an accident, for treatment of particular health conditions, for physiotherapy and so forth.

The Activity Environment Generator may be particularly advantageous in situations that entail limited space, possibly for a prolonged time such as, for example, during a flight on an airplane where lack of sufficient physical activity may have serious health consequences.

All the above, without the need for costly and cumbersome systems which are unfeasible, impractical or costly for the kind of physical exercise and associated settings contemplated in this application.

SUMMARY OF THE INVENTION

The invention relates to a method and apparatus for an Activity Environment Generator. The Activity Environment Generator provides dynamically controllable forces with which the user interacts in the course of his/her activity.

The activity may be of any kind including, for example, fall-prevention training, physiotherapy, rehabilitation, physical exercise in general, sensorimotor training, movement and balance training and so forth. The activities are also connected to psychological benefits such as reduction of anxiety.

By interacting with the forces provided by the Activity Environment Generator the User carries out desired activities, which involve—as it will be elaborated upon in the described embodiments of the invention—different parts of the body and/or different psycho/physical functionalities, according to the case.

Said activities usually requires space and equipment generally available in a gymnasium, in a clinic, in a rehabilitation center and so forth. Furthermore, some of these activities are preferably, carried out under the supervision of an instructor. Consequently, a person who wishes to carry out said activities will have often to commute in order to carry them out.

The Activity Environment Generator provides the conditions necessary for carrying out the abovementioned activities anywhere in a more convenient flexible and effective manner.

Said conditions can recreated anew with each use of the Activity Environment Generator and, hence, the term "Generator".

The Activity Environment Generator optionally enables involvement in the activity by a Remote Trainer and real-time communication between the User and the Remote Trainer.

Data and software related to the Activity Environment Generator's activities may be stored, analyzed, used and optimize using Big Data and machine-learning techniques available in the Cloud of a health, government, public or private organization.

In one aspect of the invention, the forces provided by the Activity Environment Generator are generated by a magnetic field.

In another aspect of the invention, the forces provided by The Activity Environment Generator are generated by a pneumatic actuator.

Figure 1:
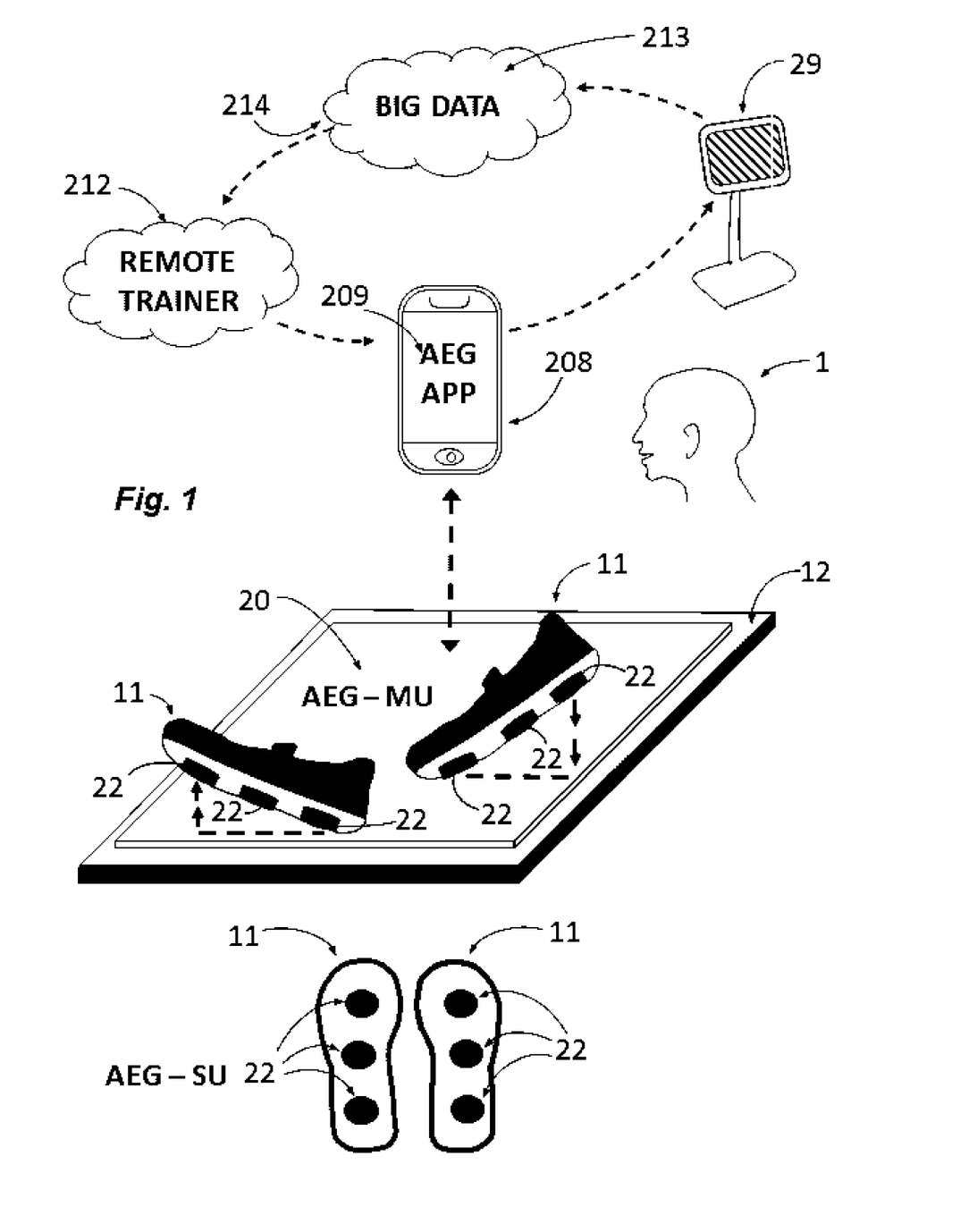

In FIG. 1, one of the many possible configurations of the Activity Environment Generator ("AEG") is schematically shown.

A number of Slave Units ("AEG-SU") indicated as 22 are included in each of a shoe-like accessory 11 that is worn by User 1 and constitutes an AEG-Wearable.

A surface 12 includes an AEG-Master Unit ("AEG-MU") indicated as 20. Surface 12 constitutes an AEG-Accessory.

The interaction between AEG-SU 22 and AEG-MU 20 creates a pull force (as shown, for illustration, in the right shoe) and/or a push force (as shown, for illustration, in the left shoe). The intensity and direction of the forces between AEG-MU 20 and AEG-SU 22 are dependent on software and/or data and, more generally, on commands generated by the AEG APPLICATION ("AEG-APP") indicated as 209 which is present in Communication Device 208 which is a mobile phone operated by User 1.

Said forces are controlled by the AEG and are such as to allow User 1 to carry out advantageously a physical activity that is related to said forces.

The above interactions and the relative input and output constitute an AEG-Session.

According to specific embodiments, a Remote Trainer 212 is connected to the AEG and can influence the course of the AEG-Session. Data (including Big Data 213) and processes that take place in Cloud 214, can also influence the course of the AEG-Session. Optionally, a Human Machine Interface ("HMI") 29 may also be included in the AEG.

As it is can be readily appreciated the AEG is easily scalable and Modular.

Furthermore, in specific embodiments a AEG-Wearable or a AEG-Accessory may be structured as to allow User 1 to add to them or remove from them one or more AEG-SU 22 and/or AEG-MU 20. This can be done by providing the AEG-Wearable and/or the AEG-Accessory with connectors that enable User 1 to connect or disconnect a number of AEG-SU 22 and/or AEG-MU 20 by, for example, plugging or unplugging them.

Since the AEG is, as already mentioned, scalable and modular, its structure in different embodiments may vary largely.

In any case, the term AEG (or "AEG 2") means, in this application, a AEG configuration that includes, at least, a single AEG-MU 20 and a single AEG-SU 22 and Power Source 210, which is always implied in all the application even when not shown. Furthermore it is stressed that obvious or non-essential elements may optionally not be described, but assumed, in this application FIG. 2 schematically shows one of the possible configurations of the apparatus according to the invention.

Figure 2:
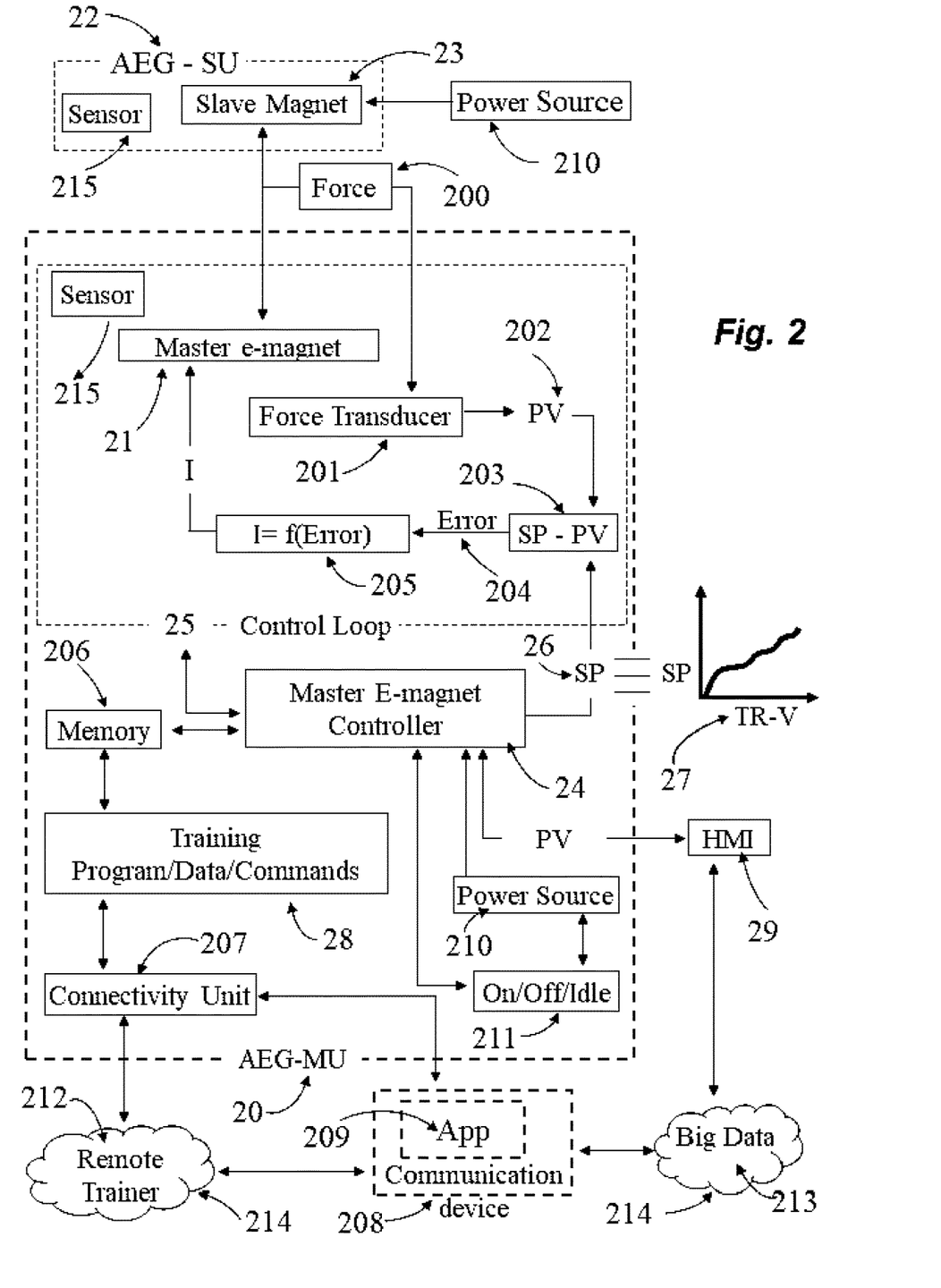

In FIG. 2, as well in all other drawings of this application, the numbers indicating any element (be said element a component, step and so forth) in the drawings of this application are either placed on the element itself or are connected to either a straight line or a curve ending with an arrow pointing to said element.

The term "element" in this application means anything pertaining to AEG 2 that is physically or functionally necessary or useful in order to carry out the invention and its specific embodiment. The term "element" includes unit/s, component's, hardware, software, processes, data and any combination thereof.

The relationship between the elements is indicated by simple or bidirectional arrows according to the case.

If FIG. 2 an Activity Environment-Generator Master Unit, or in brief "AEG-MU", or "AEG-Master Unit", is indicated as 20.

AEG-MU 20 includes a Master Electromagnet (also referred to as "Master-EM") indicated as 21. The term "Electromagnet" means a type of magnet in which the magnetic field of the magnet is produced by an electric current. The term "Master", in relation to the Master Electromagnet 21 means that, based on the commands generated by the hereafter described Master Electromagnet Controller 24, Master Electromagnet 21 is able to determine the intensity, direction and timing of the interaction with other magnets and/or other magnetizable elements, as it will be described in detail hereafter.

AEG-SU 22 includes a Slave Magnet 23, or, in brief "S-Magnet". S-Magnet 23 can be an electromagnet or a permanent magnet, depending on the requirements of each specific embodiment and on different considerations such as, size and/or weight of the AEG 2 or of elements thereof, power consumption, intensity of the magnetic field and so forth.

More generally, Slave Magnet 23 may be of any suitable kind including, for example, permanent magnets, temporary magnets, electromagnets, fix polarity magnets, reverse-polarity magnets, electromagnetic circuits, etc.

Master Electromagnet Controller 24, controls all the operations of AEG-Master Unit 20, including Control Loop 25. Master Electromagnet Controller (or, in brief, "MEM-Controller") 24 also controls, directly and/or indirectly, the operations of AEG-SU 22 and, more in general, the whole of the operations of AEG 2. The term "Controller" in relation to Master Electromagnet Controller 24, includes the terms "controller", "processor", "CPU", "microprocessor" and any combination thereof.

Reference to Master Electromagnet Controller 24 also includes all software, data and processes necessary for its operations and, furthermore, encompasses the interfacing with any hardware and/or software component, element, unit or device external to AEG-Master Unit 20. AEG-Master Unit 20 also controls or influences, directly and/or indirectly, the operations of AEG-SU 22 and, more in general, the operations of AEG 2.

The terms "Master" and "Slave" in this application relate to elements in the Activity Environment Generator 2, whereby an element (the "Master") controls one or more of the other elements (the "Slave/s") according to predefined rules, including the case in which a AEG-Master Unit transfers or shares control over one or more elements with one or more AEG-Slave Unit/s.

An external object to which a AEG-Master Unit and/or or a AEG-Slave Unit is attached to, rather than being attached to the User 1 (or being otherwise held or carried by the User 1), is referred to as an "Activity Environment Generator Accessory" or, in short, "AEG-Accessory". The "AEG-Accessory" may be any surface, object, physical medium or accessory external to User 1 to which a AEG-Master Unit and/or or a AEG-Slave Unit is/are attached to.

The term "attached", in reference to the AEG 2 or in reference to any number of its elements, means any manner in which one or more of said AEG elements is/are carried or placed, worn—thus becoming an "AEG-Wearable", strapped, stuck, mounted, fastened, tied or otherwise secured to any part of a User's body—typically, but not exclusively, to one or more of: a limb, the neck, the head, fingers, toes, knee, elbow, the jaw. The term "body" In this application means each and all physical parts of a person.

The term "attached", in relation to the manner in which an AEG-Element is attached to an AEG-Accessory or to san AEG-Wearable, also includes the terms "integral to", "built-in", "welded", "glued", "sewed" or equivalent ones.

In the case of an AEG-Accessory, an AEG element may be attached, for example, to the back of an armchair, the arms of an armchair, a mat, floor, wall, a door, an airplane seat, a sport accessory, a strap, an elastic band, a handle and so forth.

In the case of an AEG-Wearable, an AEG element may be attached, for example, to a belt, a glove, a shoe, a shirt, a collar, a sport wearable, and elastic band, a head band, a helmet and so forth.

At 26 a Setpoint, that is, the desired value for a variable, is set by Master Electromagnet Controller 24. The variable may be, for, instance the pressure between Master Electromagnet 21 and Slave Magnet 23. If this is the case, the Setpoint defines the intensity and sign of the desired Force (attractive or repulsive) between Master E-magnet 21 and Slave Magnet 23 being said Force indicated as 200. User 1 carries desired activities by interacting with Force 200 and/or with communication and/or feedback provided by AEG 2.

The Setpoint may be constant and/or predefined or it may change dynamically according to a Training Variable (or, in short, "TR-V") 27, and/or a number or Training Variables present in Training Program/Data/Commands (or, in short, "TDC") 28 and, in general, according to commands issued by Magnet E-magnet controller 24.

TDC 28 may be of any kind including ones necessary for or deriving from the operation of the AEG 2 including commands that influence the operation elements of AEG 2.

TDC 28 also includes prestored data, software, protocols, streamed data, APP 209, databases, data and calculations results of any kind and resulting, stored, originated in or acquired from elements the AEG 2 or from elements external to it. TDC 28 or parts thereof may be transmitted between one or more of the elements of AEG 2. Said transmission may be bidirectional or one-directional according, to the requirements of specific embodiments of the invention.

TDC 28, or parts, thereof may be prestored in the AEG-Master Unit 20 and/or provided through Connectivity Unit 207 and/or HMI 29, being the latter two described below.

Examples of TR-V are: attractive or repulsive force (the magnetic force between Master E-magnet 21 and Slave Magnet 23) at a given point of time, duration and timing of said forces, the distance between AEG-MU 20 and AEG-SU 22, the spatial coordinates of the AEG-MU 20 and/or the AEG-SU 22, their relative displacements etc.

Force Transducer 201 transforms Force 200 from mechanical force into an electrical signal which constitutes Process Value (or in brief, "PV") indicated as 202. Force Transducer 201 may be of any suitable kind including, for example, a strain gauge or a piezoelectric sensor.

In 203 the difference between Setpoint 26 and Process Value 202 is continuously evaluated, resulting in the error signal $\varepsilon(t)=SP-PV$. The output current I(t) will be adjusted by the Master E-magnet controller 24 in a way that that seeks to annulate the error signal value using a predetermined function ("I=f(error)") 205 whereby error=$\varepsilon(t)$.

For the sake of example, only, below is a well-known feedback control function where $C_1$, $C_2$ and $C_3$ are constants, "t" is the time and "$\varepsilon$" stands for error.

$$I(t)=C_1 \times \varepsilon(t)+C_2 \times \int \varepsilon(t)dt+C_3 \times d\varepsilon(t)/dt$$

This is known as the PID controller standard standing for Proportional-Integral-Derivative controller.

The apparatus in FIG. 2 further includes a memory 206 that for both storing data and for running commands and executing any process required by specific embodiments of the invention. Memory 206 may be, for example a Flash memory, a combination of any of Ram, Rom, NV-Ram, integrated circuit, hardwired and so forth, as long as memory 206 satisfies all the requirements of a volatile and non-volatile memory. Memory 206 may be a single component or a number of separated components that that work in conjunction. Memory 206 may, among other things, be integral to Master E-magnet controller 24 or part of the same circuit.

Memory 206 stores and/or runs, among other things, all data, commands and processes required by the invention, including those of TDC 28 and those required by Master E-magnet controller 24.

AEG-MU 20 is preferably provided with Connectivity Unit 207 which enables the communication between AEG-Master Unit 20 and any device and/or hardware and/or software component, element or unit external to AEG-Master Unit 20. Connectivity Unit 207 may use any kind of wired connection, such as USB, or HDMI and/or may use any kind of wireless connection provided by Bluetooth, Wi-Fi, and/or any kind of wireless network including one or more of: a cellular network, LANS, WLAN, PAN, MAN, WAN, internet, TV network, satellite network etc.

A Communication Device 208, for instance a cellular phone, is connected to the AEG-MU 20 though Connectivity Unit 207.

Communication Device 208 is equipped with an Application (or, in short, "App") indicated as 209 and, optionally, with any other software and/or data, including, for example TDC 28 or parts thereof, which can be used by User 1, to control all the operations of the AEG-Master Unit 20, of AEG-SU 22 and, directly and/or indirectly, the operations of AEG 2.

A limited list of features of App 209 includes the following examples:

Receiving, through suitable interface, feedback related to an AEG-Session, which feedback belonging to one or more of the following kinds: textual, graphic, audio, haptic and so forth. Said feedback, may be originated from App 209 itself and/or from Trainer 212 and/or from Cloud 214.

Changing Setpoint 26

Altering the course of the activity—increasing or decreasing difficulty. Selecting a TR-V 27.

Operating Power Source 210.

Carrying out any standard log-in and/or administrative operation (not shown in FIG. 2). Communicating and exchanging data with the organization related to cloud 214. Receiving updates for TDC 28 including files installation, backup and removal.

It is stressed that—depending on specific embodiments of the invention—the software and/or the data present in and/or used (or usable) by any two or more among Communication Device 208, App 209, HMI 29, Big Data 213, Remote Trainer 212 and Cloud 214, may be partially or entirely shared and/or overlapping and/or duplicated and/or complementary and/or substitutive and/or equivalent.

Power Source 210, which may be of any suitable kind, sustains the operations of the AEG-MU 20, the AEG-SU 22 and of all the other elements of AEG 2.

Master E-magnet controller 24 is provided with an on/off/idle functionality (211) which enables to toggle the state of AEG-MU 20 to one of said three states in response to specific predefined event such as, for example, a specific command generated by Communication Device 208, a certain interaction between AEG-MU 20 and AEG-SU 22 or a command issued by Remote Trainer 212.

AEG-MU 20 is optionally provided with a Human-Machine Interface (or, in brief "HMI") indicated as 29 which may consist of peripheral hardware and/or software for input and/or for output, including for, for example, switches, keypads, touchscreens, voice-commands generators and displays equipped with appropriate graphical user interface. HMI 29, according to the specific embodiments, may be provided in addition or in place of Communication Device 208. If provided in place of Communication Device 208, then HMI 29 is equipped either with App 209, or with a software which includes all or parts of the functionalities of App 209 and is optionally provided with connectivity capability. In both cases, said software is provided in a version that can be run in whatever operating system of the HMI 29.

HMI 29 may also consist of a computing device relative peripheral hardware and/or software for input and/or for output.

HMI 29 works in conjunction with AEG-MU 20 in a manner that allows transmission and/or use of TDC 28.

Remote Trainer 212 may be, a professional such as a doctor or a physiotherapist or a nurse, a training companion or any other person, that assists, monitors or, otherwise, participates or is involved in AEG-Session and/or in connection with said AEG-Session, before and/or after the AEG-Session itself. The term "AEG-Session", in this context, means any activity which is carried out using AEG 2 and/or in connection with the use of AEG 2 and/or in connection with the processes and data related to said use.

Remote Trainer 212 may be equipped with a Communication Device 209 and APP 208 or with HMI 29 or an equivalent equipment. Using said equipment, Remote Trainer 212 can communicate with APP 209 and/or Big Data 213 and/or HMI 29 and is afforded a wide range of possibilities that include, among other things, the following ones:

To monitor the AEG-Session carried out by User 1 and receive feedback related to said AEG-Session.

To influence Control Loop 25;

To change Force 200 in intensity and/or direction; To change one or more Training Variables 27; To use any portion of TDC 28;

Communicate with User 1 by graphic and/or text and/or voice communication; Provide User 1 with feedback;

Receiving data and/or sending data related to the AEG-Session to and/or from Cloud 214.

Consequently, Remote Trainer 212 can control—given of course that she/he is provided with the necessary authorizations as set in AEG 2—varied aspects of the AEG-Session.

For example, according to the invention Remote Trainer 212 determine the intensity and direction of Force with which User 1 interacts in the course of the AEG-Session. Further, Remote Trainer 212 can choose from TDC 28 a specific training program which contains specific exercises to be carried out in the course of the AEG-Session. Additionally, if a plurality of AEG-MU 20, and/or AEG-SU 22, HMI 29, and more than a single User 1, are involved in a AEG-Session, Remote Trainer 212 can determine the operations for each of these and coordinate the operations of each of said elements.

Cloud 214 is a public, private or semi-private cloud network cloud.

Preferably, Cloud 214 is enabled with cloud-computing features and/or machine-learning capability.

Examples of Cloud 214 include, according specific embodiments of the invention, clouds associated to any public and/or a private organization such as a hospital, a university, a government organization, a health service which organizations hold information in form of Big Data 213. Unless otherwise stated, the term "Cloud" includes the term "Big Data".

Big Data 213 includes data of any of the above mentioned public and/or a private organization. Big Data 213 may be dynamically updated. Consequently, an AG-Session can be enhanced from dynamically accumulated data and help User 1 and/or Trainer 212 and/or AEG 2 directly, without the involvement of User 1 and/or Trainer 212.

For example, TDC 28 may be frequently updated following analyses from data received in the course of an AEG-Session and/or from other medical, clinical or different kind of data provided by an organization relative to which Big Data 213 is accumulated, update or, otherwise, accumulated.

Big Data 213 may also serve as a valuable source of information for medical, clinical, logistic, statistical and administrative purposes which allow the organization, to which Big Data 213 pertains, to better plan and administer services and treatments both on micro and macro scale and improve customer-service-supplier relationship by better individually targeted treatment and attention.

For instance, accumulated data received from AEG-Sessions may show that an activity, carried out by one or more User 1 over a course of time, has demonstrated positive results in relation to a specific User 1 or a plurality of Users 1. Conversely, Big Data 213 may indicate that changes are required and point to possible required modifications, for example, in TCD 28.

Thus, for instance, if one or more User 1 has/have carried out an activity designed to improve his/their balance, following reoccurring falls, by exercising his/her feet and toes, and accumulated data over a certain time span shows a reduction in the occurrence of falls, the activity which has been proven beneficial may be continued for the same one or more User 1 and may, also, be prescribed, preventively, to other persons with a medical profile similar to User 1, even is said persons have not suffered yet of any significant lack of balance or actual falls.

Figure 3:
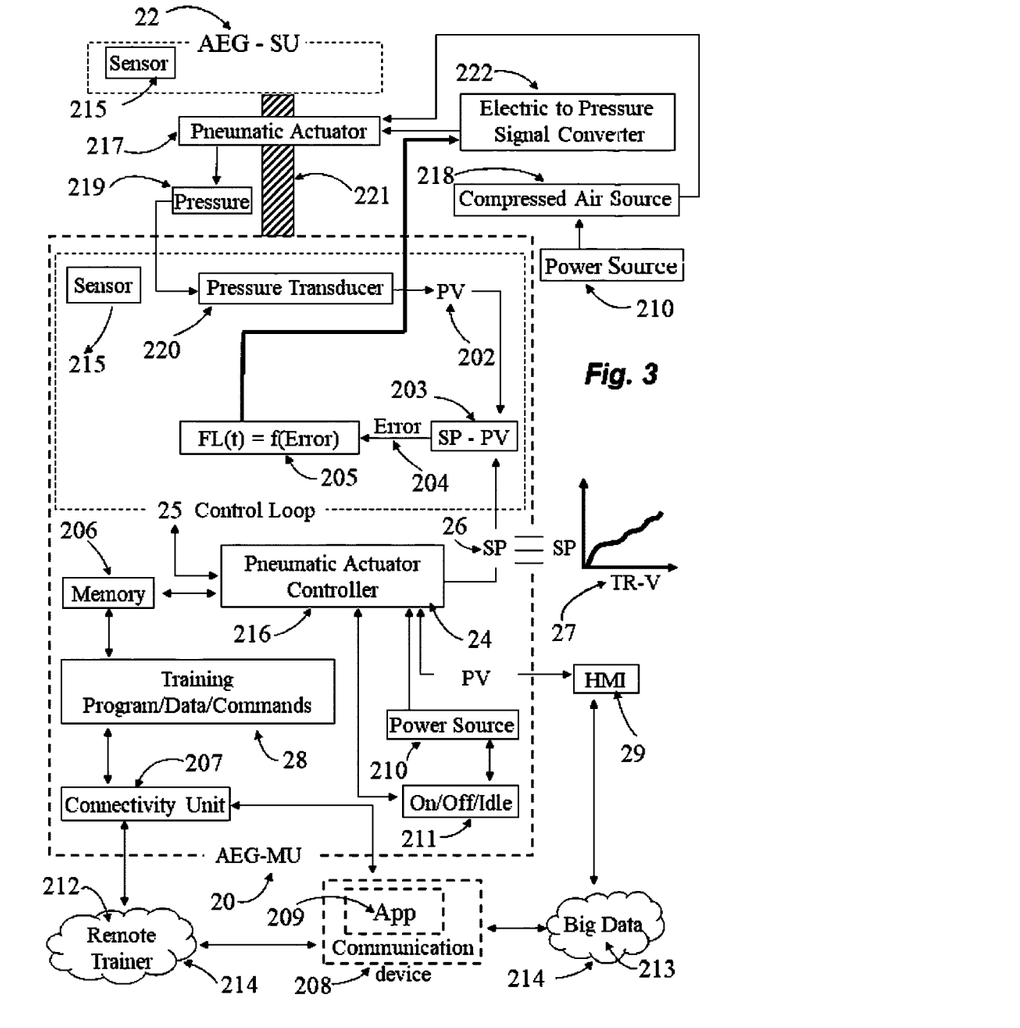

FIG. 3 Shows one of the many possible variations of the invention.

This variation involves interaction with pneumatic pressure between AEG-MU 20 and AEG-SU 23 instead of and interaction with magnetic force.

Pneumatic Actuator Controller 216 replaces Master E-magnet controller 24.

Pneumatic Actuator 217 replaces Master e-magnet 21 and Slave magnet 23.

Pneumatic Actuator 217 may have, among other things, lineal and/or rotatory capabilities.

Pneumatic Actuator 217, may be, for the sake of example only, a Mini Pneumatic Actuator (having a bore size as small as 5-10 mm.) connected to a Compressed Air Source 218 which is, optionally, connected to a Power Source 210.

Pneumatic Actuator 217, produces Pressure 219 which is transformed by Pressure Transducer 220 from mechanical force into an electrical signal which constitutes Process Value (or in brief, "PV") indicated as 202. In this variation of the invention, Setpoint 26 provided by Pneumatic Actuator Controller 216, is a pressure value.

The output air flow denoted as FL(t) will be adjusted using a predetermined function FL(t)=f(error) 205.

In this variation of the invention a sample feedback control function could be $$FL(t)=C_1\times\varepsilon(t)+C_2\times\int\varepsilon(t)dt+C_3\times d\varepsilon(t)/dt$$

Where C1, C2 and C3 are constants and FL(t) is the air flow and "t" is the time and "ε" stands for the error.

Then, the computed air flow value is converted from an electrical signal into an air flow signal by Electric to Pressure Signal Converter 222, that regulates the air flow inside Pneumatic Actuator 217 thus adjusting the pressure generated by Compressed Air Generator 218 to the desired pressure into Pneumatic Actuator 217.

Similarly to what described in connection of FIG. 2, the Setpoint may be constant and/or predefined or it may change dynamically according to a Training Variable (or, in short, "TR-V") 27, and/or a number or Training Variables present in Training Program/Data/Commands (or, in short, "TDC") 28 and, in general, according to commands issued by Pneumatic Actuator Controller 216.

In according to this variation of the invention a physical connection, indicated as 221, must be provided between AEG-MU 20 and AEG-SU 22 in order to enable Pneumatic Actuator 218 to act on AEG-MU 20 and AEG-SU 22.

Apart from what described above, the remaining elements of the AEG 2 in FIG. 3 are the same as the elements of the AEG 2 in FIG. 2.

In addition to what described above, one or more kinds of sensors may optionally be provided in order to measure the distance and/or position and/or speed between AEG-MU 20 and AEG-SU 22.

This may be useful in order to accurately follow the activity of User 1 and, for instance, better determine the trajectory followed in the course of an activity, the number of repetition of a certain activity (for instance a movement of a part of the body) and so forth.

Alternatively and optionally, the distance between AEG-MU 20 and AEG-SU 22 be estimated and/or calculated in Loop 25 based on the resulting pattern of errors found in 203 considering, for instance, the error over a lapse of time, whereby a certain range of error values may be indicative of limited movements over said lapse of time.

Examples out of a wide range of sensors include, according to each specific embodiment: distance transducers, distance sensors, tilt sensors, ultrasonic sensors, position sensors, magnetic position switches, proximity sensors, mechanical switches, variable reluctance sensors etc.

Additional variations of the inventions may use different kinds of force generators, other than the electromagnetic or pneumatic ones described in relation to FIG. 1 to FIG. 3, as long as such force generators are suitable for AEG2.

Also, according to additional variations of the invention certain elements, as for example, Control Loop 25 and Force Transducer 201 of AEG 2, could, optionally, be implemented in analog form.

Before the description proceeds the following points should be stressed out:

The description above of FIG. 2 and FIG. 3 configurations of AEG 2 with a single AEG-MU 20 and a single AEG-SU 22. However, the invention allows the use of multiple AEG-MU 20 and/or of multiple AEG-SU 22 in an AEG 2 in any desired combination and configuration. Thus, according to different specific embodiments, an AEG may include a single AEG-MU 20 and several AEG-SU 22, an array of AEG-MU 20 and an array of AEG-SU 22 having the same number of elements in each array and so forth.

Furthermore, as it will be described in one of the preferred embodiments, the configuration of MG 1 may be easily modified making the invention easily scalable.

Figure 4:
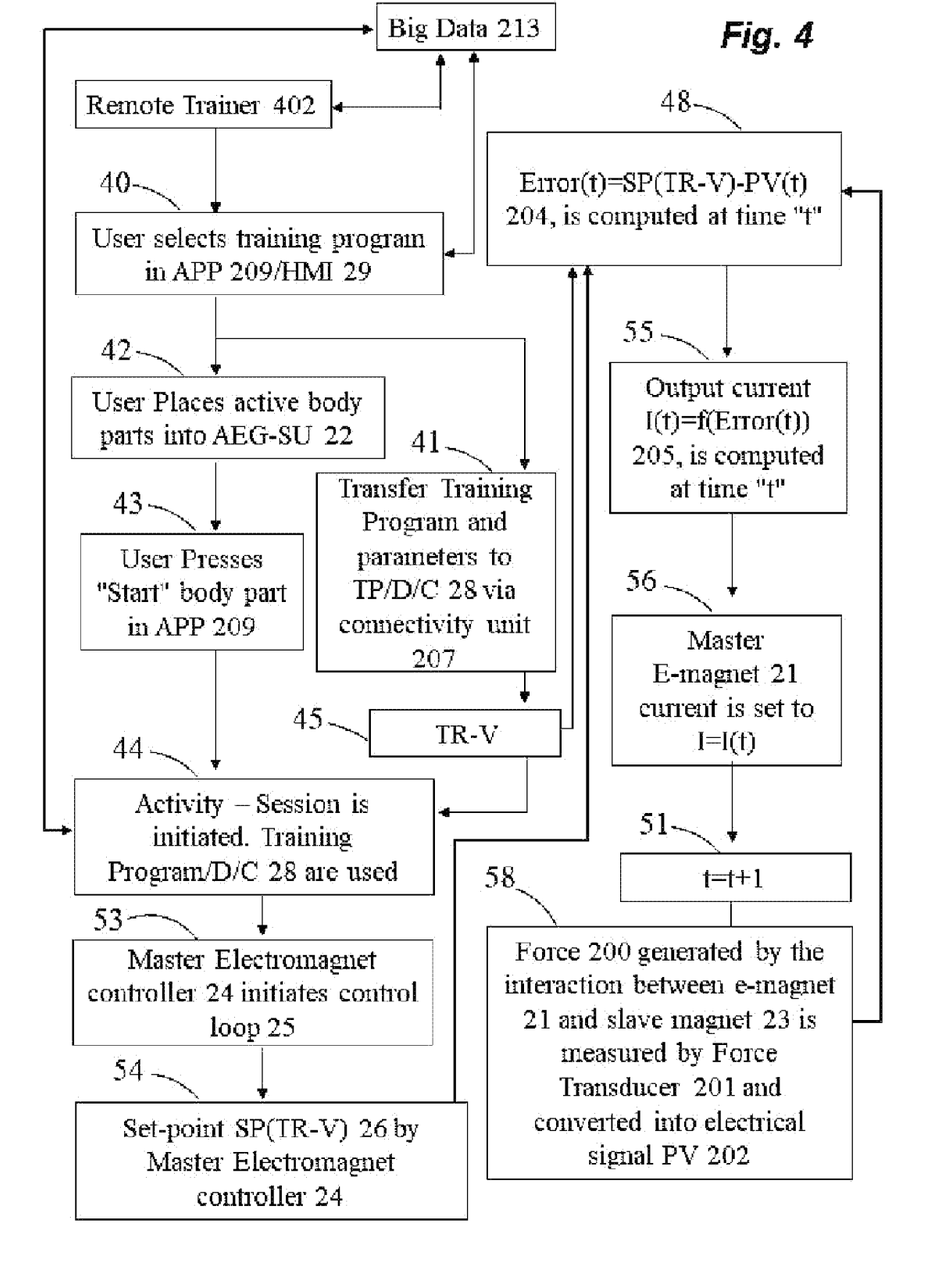

FIG. 4 shows schematically the method of the invention relative to the apparatus description in FIG. 2.

At step 40 the training program for the AEG-Session is selected in APP 209 or in the HMI 29 or by Remote Trainer 212. Big Data 213 is available.

At step 41 Transfer Training program and parameters to TP/D/C 28 takes optionally place via connectivity unit 207.

At step 42 or, optionally, before step 40, User 1 Places active body part into AEG-SU 22. At 43 User 1 starts the AEG-Session designed to train a body part using APP 209.

At 44 TP/D/C 28 Initiates the training program which can controlled by Remote Trainer 212 and which can be modified, at all times, according to changes in Big Data 213.

At 45 Training Variable 27 is set.

Master e-Magnet controller 24 Initiates Control Loop 25 at step 53

Set-point SP(TR-V) 26 is determined by Master e-magnet controller 24 at step 54

At step 48 Error(t)=SP(TR-V)-PV(t) 204, is computed at time "t".

At 55 Output current I(t)=f(Error(t)) 205, is computed at time "t".

Master e-magnet 21 Current is set to I=I(t) at step 56.

Time counter moves up at 51.

At step 58 Force 200 generated by the interaction between e-magnet 21 and slave magnet 23 is measured by Force Transducer 201 and converted into electrical signal PV 202.

Figure 5:
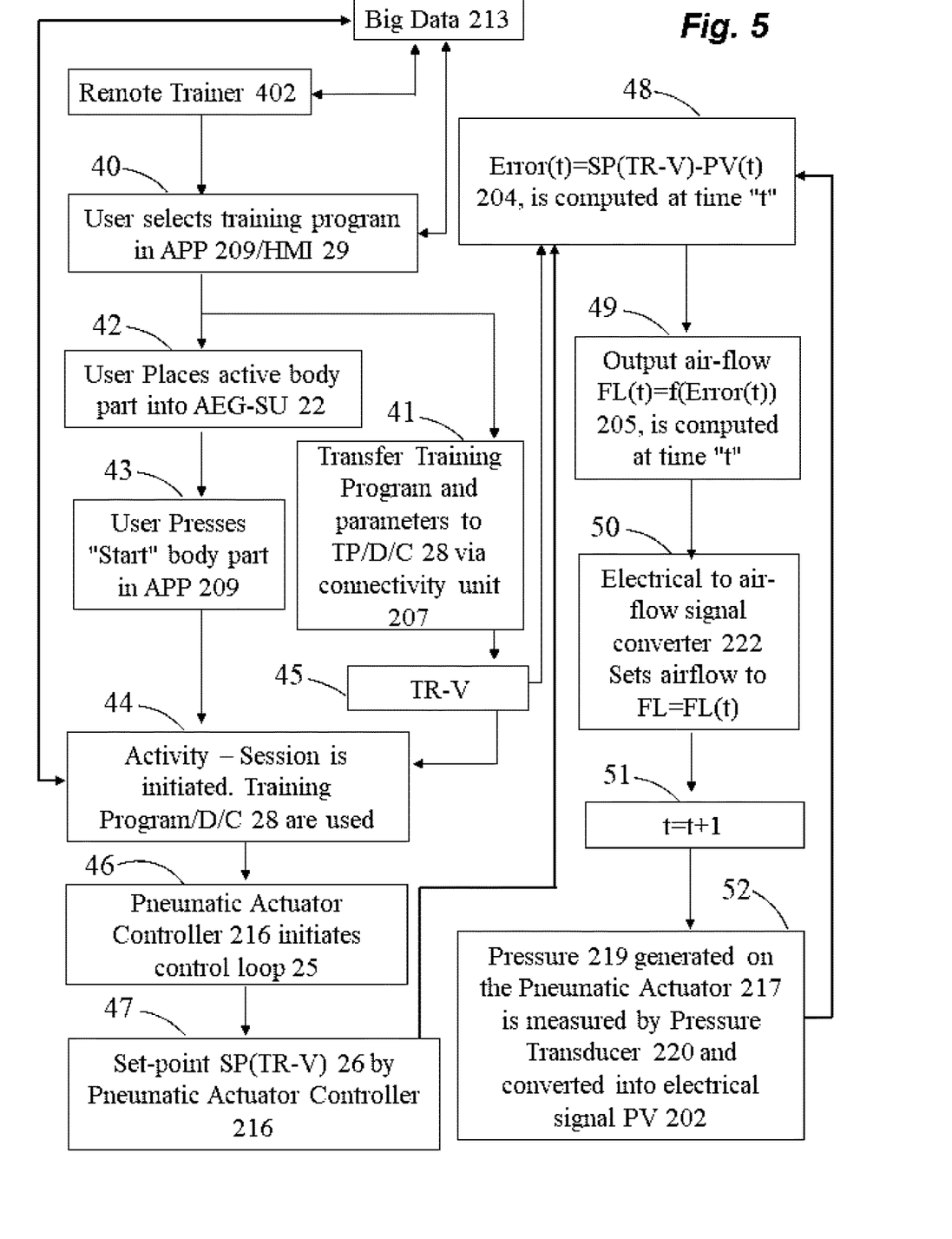

FIG. 5 shows schematically the method of the invention relative to the apparatus description in FIG. 3.

At step 40 the training program for the AEG-Session is selected in APP 209 or in the HMI 29 or by Remote Trainer 212. Big Data 213 is available.

At step 41 Transfer Training program and parameters to TP/D/C 28 takes optionally place via connectivity unit 207.

At step 42 or, optionally, before step 40, User 1 Places active body part into AEG-SU 22.

At 43 User 1 starts the AEG-Session designed to train a body part using APP 209.

At 44 TP/D/C 28 Initiates the training program which can controlled by Remote Trainer 212 and which can be modified, at all times, according to changes in Big Data 213.

At 45 Training Variable 27 is set.

Pneumatic Actuator Controller 216 initiates Control Loop 25 at step 46.

Set-point SP(TR-V) 26 by is determined by Pneumatic Actuator Controller 216 at step 47.

At step 48 Error(t)=SP(TR-V)-PV(t) 204, is computed at time "t".

At 49 Output air-flow FL(t)=f(Error(t)) 205, is computed at time "t".

Electric to air-flow signal converter 222 Sets airflow to FL=FL(t) at step 50.

Time counter moves up at 51.

At step 52 Pressure 219 generated on the Pneumatic Actuator 217 is measured by Pressure Transducer 220 and converted into electrical signal PV 202.

ADDITIONAL PREFERRED EMBODIMENTS OF THE INVENTION

Figure 6:
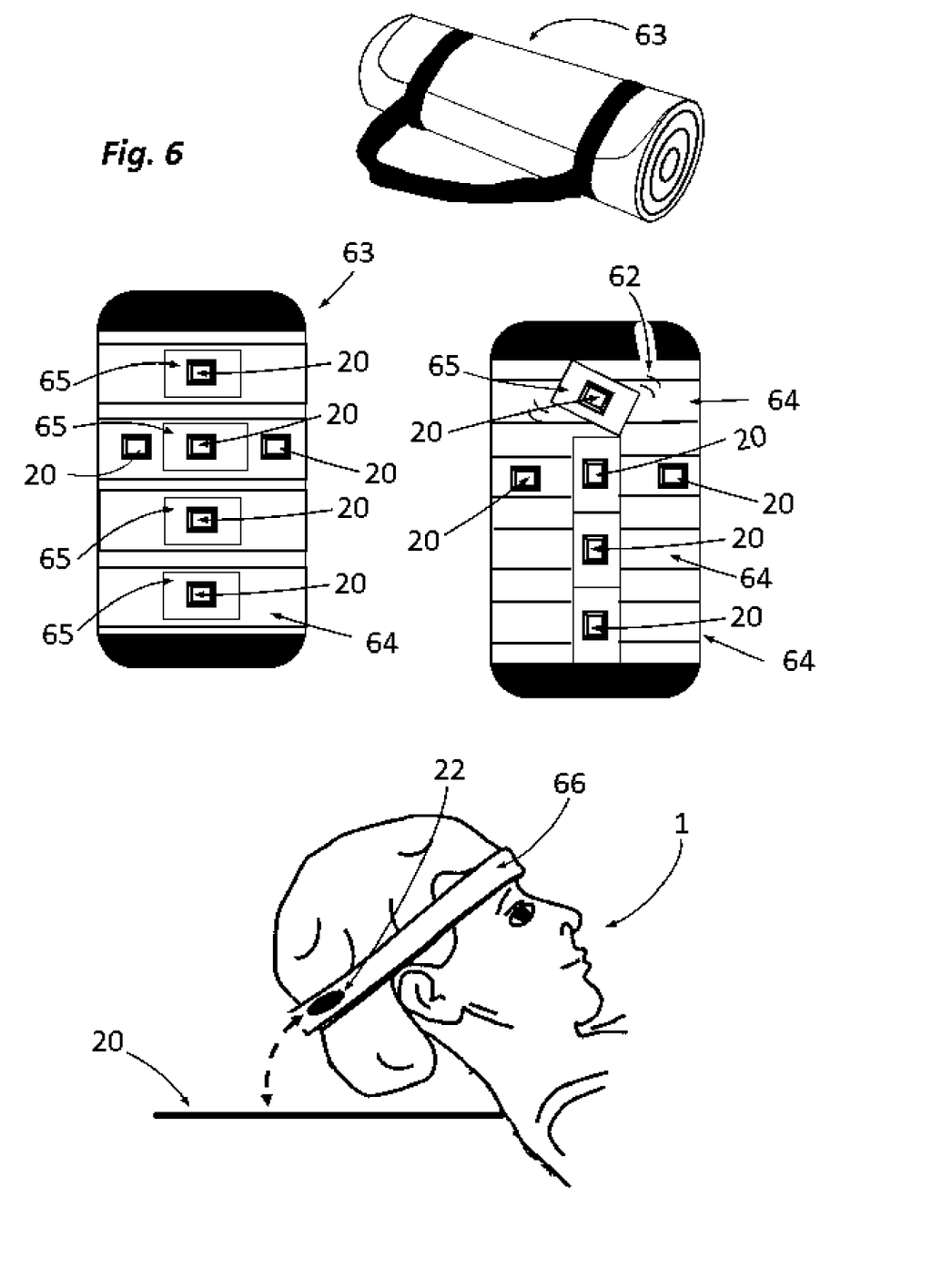

FIG. 6 show and exercise mat 63 which resembles a yoga mat. A number of element 64 which preferably have some degree of rigidity are provided. An arrangement that allow rigid or semi-rigid elements 65, also provided, to be joined together, is shown at 62. Elements 65 are provided each with a desired number of AEG-MU 20.

User 1 wears a head band 66 which constitute both a AEG-Wearable and an AEG-Accessory.

Head band 66 is equipped with AEG-SU 22 that interacts with AEG-MU 20 on that mat 63 thus creating the conditions for exercise of the neck.

Figure 7:
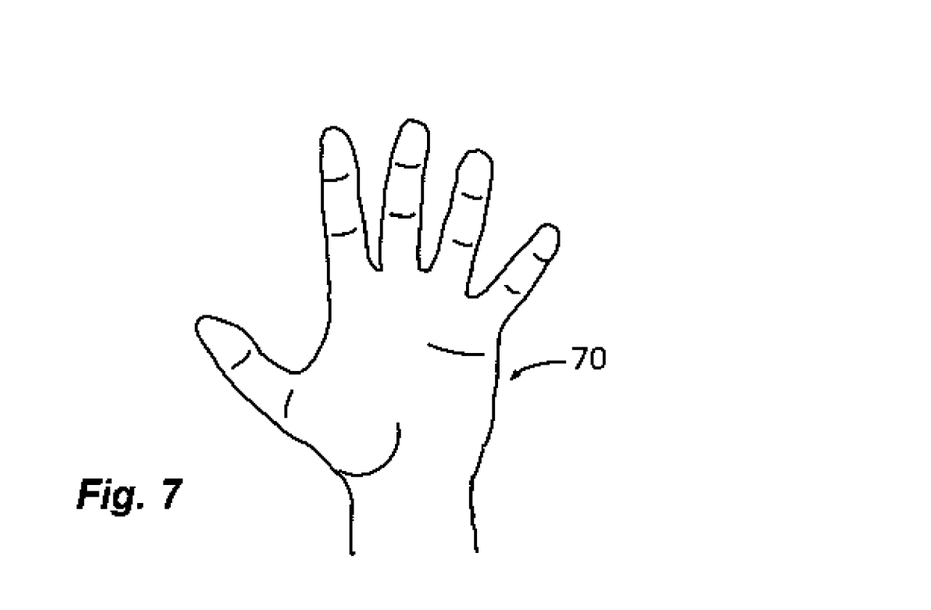

In FIG. 7, 71 is a schematic representation of hand 70 with a numbers of AEG-Wearables 72 on it. Each AEG-Wearable on the fingers has one or more AEG-SU 22 whereas AEG-Wearables 72 on the palm of the hands include a AEG-MU 20. This arrangement Generates an Activity Environment suitable for exercise of the fingers and of the hand.

The AEG-Wearables 72 may be attached or each may be physically separate but in interaction.

Furthermore, in one variation, the AEG-Wearables are joined together and provide a frame on which AEG-MU 20 and/or AEG-SU may be plugged or removed from with a significant degree of scalability and modularity.

Figure 8:
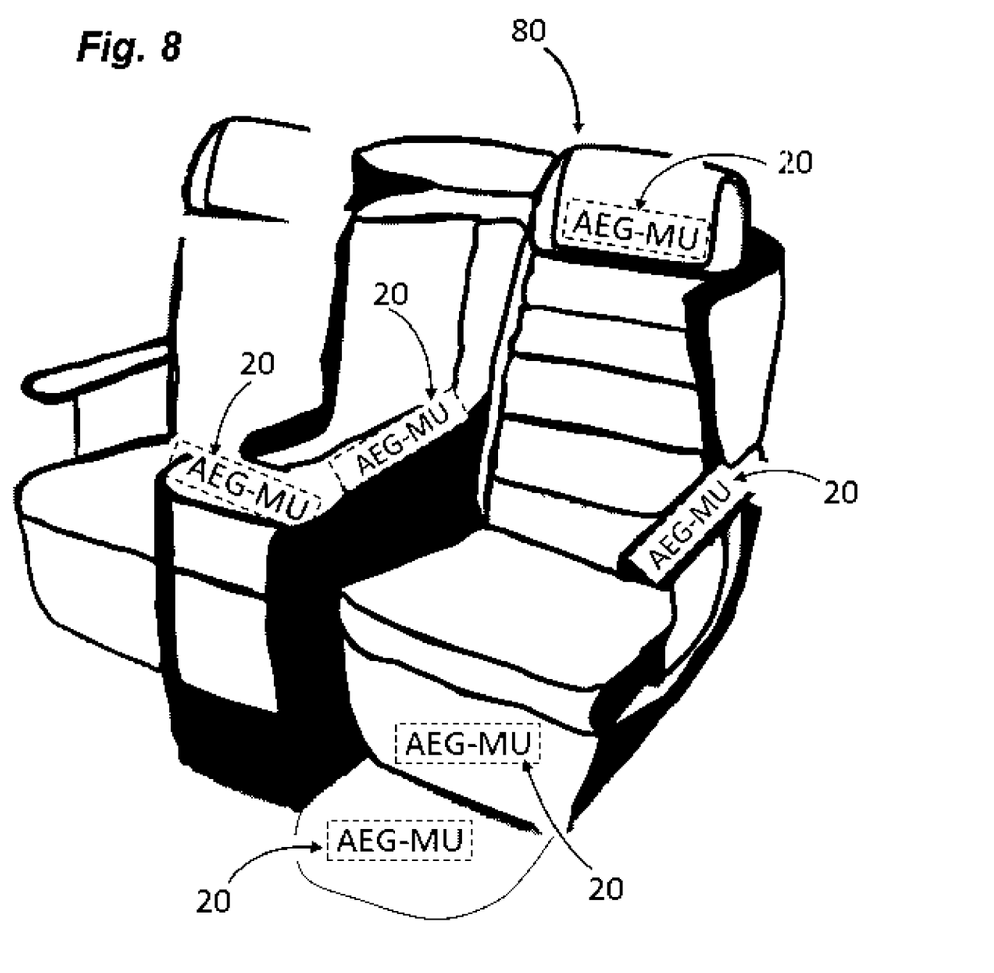

FIG. 8 shows an airplane sit 80 that constitutes an AEG-Accessory to which a number of AEG-MU 20 are attached or built in. A User 1 wearing a AEG-Wearable containing a number of AEG-SU 22 can carry out a AEG-Session while flying with the advantage to reduce the risks involved in prolong inactivity during a flight.

To conclude, it may be useful to note that in all embodiments Remote Trainer 212 has the possibility to change, through an appropriate interface, the forces experience by User 1.

A significant and useful implication of this fact is that Remote Trainer 212 may demonstrate in a tangible manner an exercise or a movement to User 1 without using any predetermined training setting, as if Remote Trainer 212 were present and within reach of User 1.

While a number of preferred embodiments have been described it is stressed that a vast number of additional embodiments are available by the invention.

Furthermore, elements of the invention may be changed, rearranged in different configurations and they, or equivalent ones, may be added or removed without changing the scope of the invention and of the appended claims.

The invention claimed is:

1. An Activity Environment Generator (AEG) apparatus for the exercise of specific body areas of a user and, in particular, for wellness, rehabilitation, physiotherapy, injury prevention, fall prevention, and training in general; the AEG apparatus including:
   i. one or more AEG-Master Unit/s (AEG-MU), which AEG-MU each includes one or more master electromagnet/s;
   ii. one or more AEG Slave Units (AEG-SU), which AEG-SU each includes a slave magnet;
   iii. a master electromagnet controller that controls all operations of the AEG-MU, including a control loop and an attractive or repulsive force between the master electromagnet/s and slave magnet, wherein the AEG apparatus is capable of applying force in both directions along an axis of motion;
   iv. a force transducer;
   v. software for carrying out a session of the AEG apparatus including changing the attractive or repulsive force between the AEG-MU and the AEG-SU based on an error generated by the control loop;
   vi. memory for both storing data and for running commands and executing any required process, including those of a software application; and
   vii. a connectivity unit which enables communication between the AEG-Master Unit and other elements including with a communication device, a remote trainer, a cloud, big data in a cloud, and a human machine interface.

2. The apparatus according to claim 1, wherein the AEG apparatus is capable of applying force along multiple axes of motion.

3. The apparatus according to claim 2, wherein at least one element of the AEG apparatus is attached to at least one part of the user's body, said part is typically, but not exclusively: a limb, the neck, the head, fingers, toes, a knee, an elbow, or the jaw.

4. The apparatus according to claim 2, wherein at least one AEG element out of the following: the AEG-MU, the AEG-SU, the master electromagnet controller, the force transducer, the memory, the connectivity unit, or the human machine interface, is attached to an external object rather than being attached to the user, and wherein said external object is, typically but not exclusively, one of: a mat, any floor-like surface, a seat, the back of an armchair, an airplane seat, a TV chair, an office chair, a train seat, a wall, a door, any surface, or a domestic or an hospital bed.

5. The apparatus according to claim 2, wherein a number of AEG-MU are attached to an airplane seat and a number of AEG-SU are attached to the user.

6. The apparatus according to claim 2, wherein said apparatus is structured as an exercise mat and comprises:
   i. a first set of two or more physical elements, each of said first set of physical elements being optionally provided with one or more AEG-MU;
   ii. a second set of two or more physical elements, each of said second set of physical elements being moveable and provided with one or more AEG-MU;
   iii. an arrangement that allows the first set of physical elements and the second set of physical elements to be joined together; and
   iv. a head band to be worn by the user, said head band being equipped with at least one AEG-SU capable of interacting with the AEG-MU on the exercise mat.

7. The apparatus according to claim 2, wherein the AEG apparatus is suitable for exercise of the fingers and of the hand, and the AEG apparatus comprises:
   i. an AEG-MU attached to the palm of the hands; and
   ii. one or more AEG-SU attached to the fingers;
   wherein said AEG-MU and said AEG-SU are either physically attached or separate, but in interaction.

8. The apparatus according to claim 1, wherein the AEG apparatus is modular and capable of applying force differentially to specific parts of the user in relation to other parts of the body of said user when all master electromagnets and slave magnets are attached to parts of the body of said user.

9. The apparatus according to claim 8, wherein at least one element of the AEG apparatus is attached to at least one part of the user's body, said part is typically, but not exclusively: a limb, the neck, the head, fingers, toes, a knee, an elbow, or the jaw.

10. The apparatus according to claim 8, wherein at least one AEG element out of the following: the AEG-MU, the AEG-SU, the master electromagnet controller, the force transducer, the memory, the connectivity unit, or the human machine interface, is attached to an external object rather than being attached to the user, and wherein said external object is, typically but not exclusively, one of: a mat, any floor-like surface, a seat, the back of an armchair, an airplane seat, a TV chair, an office chair, a train seat, a wall, a door, any surface, or a domestic or an hospital bed.

11. The apparatus according to claim 8, wherein a number of AEG-MU are attached to an airplane seat and a number of AEG-SU are attached to the user.

12. The apparatus according to claim 8, wherein said apparatus is structured as an exercise mat and comprises:
   i. a first set of two or more physical elements, each of said first set of physical elements being optionally provided with one or more AEG-MU;
   ii. a second set of two or more physical elements, each of said second set of physical elements being moveable and provided with one or more AEG-MU;
   iii. an arrangement that allows the first set of physical elements and the second set of physical elements to be joined together; and
   iv. a head band to be worn by the user, said head band being equipped with at least one AEG-SU capable of interacting with the AEG-MU on the exercise mat.

13. The apparatus according to claim 8, wherein the AEG apparatus is suitable for exercise of the fingers and of the hand, and the AEG apparatus comprises:
   i. an AEG-MU attached to the palm of the hands; and
   ii. one or more AEG-SU attached to the fingers;
   wherein said AEG-MU and said AEG-SU are either physically attached or separate, but in interaction.

14. The apparatus according to claim 1, wherein the AEG apparatus allows setting specific motion patterns which support the desired motion and limit other movements in a way that is modifiable during the exercise session.

15. The apparatus according to claim 14, wherein at least one element of the AEG apparatus is attached to at least one part of the user's body, said part is typically, but not exclusively: a limb, the neck, the head, fingers, toes, a knee, an elbow, or the jaw.

16. The apparatus according to claim 14, wherein at least one AEG element out of the following: the AEG-MU, the AEG-SU, the master electromagnet controller, the force transducer, the memory, the connectivity unit, or the human machine interface, is attached to an external object rather than being attached to the user, and wherein said external object is, typically but not exclusively, one of: a mat, any floor-like surface, a seat, the back of an armchair, an airplane seat, a TV chair, an office chair, a train seat, a wall, a door, any surface, or a domestic or an hospital bed.

17. The apparatus according to claim 14, wherein a number of AEG-MU are attached to an airplane seat and a number of AEG-SU are attached to the user.

18. The apparatus according to claim 14, wherein said apparatus is structured as an exercise mat and comprises:
   i. a first set of two or more physical elements, each of said first set of physical elements being optionally provided with one or more AEG-MU;
   ii. a second set of two or more physical elements, each of said second set of physical elements being moveable and provided with one or more AEG-MU;
   iii. an arrangement that allows the first set of physical elements and the second set of physical elements to be joined together; and
   iv. a head band to be worn by the user, said head band being equipped with at least one AEG-SU capable of interacting with the AEG-MU on the exercise mat.

19. The apparatus according to claim 14, wherein the AEG apparatus is suitable for exercise of the fingers and of the hand, and the AEG apparatus comprises:
   i. an AEG-MU attached to the palm of the hands; and
   ii. one or more AEG-SU attached to the fingers;
   wherein said AEG-MU and said AEG-SU are either physically attached or separate, but in interaction.

20. The apparatus according to claim 1, wherein the slave magnet is one of the following kinds: magnets, temporary magnets, electromagnets, fixed polarity magnets, reverse-polarity magnets, or electromagnetic circuits.

21. The apparatus according to claim 1, wherein the transducer is one of the following: a strain gauge, a piezo-electric sensor or a pressure transducer or an equivalent, either digital or analog.

22. The apparatus according to claim 1, wherein at least one element of the AEG apparatus is attached to at least one part of the user's body, said part is typically, but not exclusively: a limb, the neck, the head, fingers, toes, a knee, an elbow, or the jaw.

23. The apparatus according to claim 1, wherein at least one AEG element out of the following: the AEG-MU, the AEG-SU, the master electromagnet controller, the force transducer, the memory, the connectivity unit, or the human machine interface, is attached to an external object rather than being attached to the user, and wherein said external object is, typically but not exclusively, one of: a mat, any floor-like surface, a seat, the back of an armchair, an airplane seat, a TV chair, an office chair, a train seat, a wall, a door, any surface, or a domestic or an hospital bed.

24. The apparatus according to claim 1, wherein the AEG apparatus is provided with at least one of the following types of sensors for evaluating movements of the user: distance transducers, distance sensors, tilt sensors, ultrasonic sensors, position sensors, magnetic position switches, proximity sensors, mechanical switches, or variable reluctance sensors.

25. The apparatus according to claim 1, wherein a number of AEG-MU are attached to an airplane seat and a number of AEG-SU are attached to the user.

26. The apparatus according to claim 1, wherein said apparatus is structured as an exercise mat and comprises:
   i. a first set of two or more physical elements, each of said first set of physical elements being optionally provided with one or more AEG-MU;
   ii. a second set of two or more physical elements, each of said second set of physical elements being moveable and provided with one or more AEG-MU;
   iii. an arrangement that allows the first set of physical elements and the second set of physical elements to be joined together; and
   iv. a head band to be worn by the user, said head band being equipped with at least one AEG-SU capable of interacting with the AEG-MU on the exercise mat.

27. The apparatus according to claim 1, wherein the AEG apparatus is suitable for exercise of the fingers and of the hand, and the AEG apparatus comprises:
   i. an AEG-MU attached to the palm of the hands; and
   ii. one or more AEG-SU attached to the fingers;
   wherein said AEG-MU and said AEG-SU are either physically attached or separate, but in interaction.

28. The apparatus according to claim 27, wherein the AEG-MU and the AEG-SU are joined by a frame and on which frame the AEG-MU or the AEG-SU may be plugged or removed from.

29. A method for exercising specific body areas of a user using an activity environment generator (AEG) and, in particular, for wellness, rehabilitation, physiotherapy, injury prevention, fall prevention, and training in general, the method including the following steps:
   i. selecting a training program for the AEG apparatus;
   ii. optionally, transmitting training program/data/commands (TDC), or parts of said TDC, via a connectivity unit, wherein said TDC, or parts thereof, may be prestored in AEG Master Unit/s (AEG-MU), which are disposed in the AEG apparatus and/or derive from operation of the AEG apparatus;
   iii. placing an active body part of the user into AEG Slave Unit/s (AEG-SU), wherein the AEG-SU each includes a slave magnet;
   iv. starting an AEG session using a software application or other available method;
   v. setting a training variable;
   vi. initiating a control loop;
   vii. via a master electromagnet controller determining a set-point SP(TR-V), wherein "SP" stands for "set-point" and "TR-V" stands for "training variable";
   viii. computing Error(t)=SP(TR-V)-PV(t) at time "t", wherein "PV" stands for "Process Value";
   ix. computing output current I(t)=f(Error(t)) at time "t", wherein "I(t)" stands for "output current", "f" stands for "function", and "t" stands for "time";
   x. setting a master electromagnet current to I=I(t);
   xi. moving up a time counter;
   xii. measuring an attractive or repulsive force generated by interaction between a master electromagnet and the slave magnet by the force transducer, wherein the AEG apparatus is capable of applying force in both directions along an axis of motion; and
   xiii. converting force into an electrical signal.

30. The method according to claim 29, wherein the AEG apparatus is capable of applying force along multiple axes of motion.

31. The method according to claim 30, wherein a doctor, a physiotherapist, or any person other than the user who assists, monitors or otherwise participates or is involved in the AEG session, is able to perform at least one of the following:
   i. communicate with a software application;
   ii. influence the control loop;
   iii. change the intensity and/or direction of force with which the user interacts in the course of the AEG session;
   iv. change one or more training variables; or v. use any portion of the training program/data/commands (TDC).

32. The method according to claim 29, wherein the AEG apparatus is modular and capable of applying force differentially to specific parts of the user in relation to other parts of the body of said user when all the AEG-MU and all the AEG-SU of the AEG are attached to parts of the body of said user.

33. The method according to claim 32, wherein a doctor, a physiotherapist, — or any person other than the user who assists, monitors, or otherwise participates or is involved in the AEG session, is able to perform at least one of the following:
   i. communicate with a software application;
   ii. influence control loop;
   iii. change the intensity and/or direction of force with which the user interacts in the course of the AEG session;
   iv. change one or more training variables; or
   v. use any portion of the training program/data/commands (TDC).

34. The method according to claim 29, wherein the method allows setting specific motion patterns which support the desired motion and limiting other movements in a way that is modifiable during the exercise session.

35. The method according to claim 34, wherein a doctor, a physiotherapist, or any person other than the user who assists, monitors, or otherwise participates or is involved in the AEG session is able to perform at least one of the following:
   i. communicate with a software application;
   ii. influence control loop;
   iii. change the intensity and/or direction of force with which the user interacts in the course of the AEG session;
   iv. change one or more training variables; or
   v. use any portion of the training program/data/commands (TDC).

36. The method according to claim 29, wherein the function in step ix is the feedback control function:
$I(t)=C_1 \times \varepsilon(t)+C_2 \times \varepsilon(t)dt+C_3 \times d\varepsilon(t)/dt$
where $C_1$, $C_2$ and $C_3$ are constants, $I(t)$ is the current, "t" is the time, and "$\varepsilon$" stands for error.

37. The method according to claim 29, wherein a doctor, a physiotherapist, or any person other than the user who assists, monitors, or otherwise participates or is involved in the AEG session, is able to perform at least one of the following:
   i. communicate with a software application;
   ii. influence the control loop;
   iii. change the intensity and/or direction of force with which the user interacts in the course of the AEG session;
   iv. change one or more training variables; or
   v. use any portion of the training program/data/commands (TDC).

38. A method for exercising specific body areas of a user using an Activity Environment Generator (AEG) apparatus and, in particular, for wellness, rehabilitation, physiotherapy, injury prevention, fall prevention, and training in general, the method including the following steps:
   i. selecting a training program for the AEG apparatus;
   ii. optionally, transmitting training program/data/commands (TDC) or parts of said TDC via a connectivity unit, wherein said TDC, or parts thereof, may be prestored in AEG Master Unit/s (AEG-MU), which are disposed in the AEG apparatus, and/or derive from operation of the AEG apparatus;
   iii. placing an active body part of the user into AEG Slave Unit/s (AEG-SU);
   iv. starting an AEG session using a software application or other available method;
   v. setting a training variable;
   vi. initiating a control loop;
   vii. via a pneumatic actuator controller determining a set-point SP(TR-V), whereby "SP" stands for "set-point" and "TR-V" stands for "training variable";
   viii. computing Error(t)=SP(TR-V)-PV(t) at time "t", wherein "PV" stands for "Process Value";
   ix. computing output air-flow FL(t)=f(Error(t)) at time "t", wherein "FL" stands for "air flow";
   x. via an electric to air-flow signal converter setting airflow to FL=FL(t);
   xi. moving up a time counter;
   xii. measuring pressure generated on a pneumatic actuator by a pressure transducer, wherein the AEG apparatus is capable of applying pressure in both directions along an axis of motion; and
   xiii. converting pressure into an electrical signal.

39. The method according to claim 38 whereby the function in step ix is the feedback control function:
$FL(t)=C_1 \times \varepsilon(t)+C_2 \times \varepsilon(t)dt+C_3 \times d\varepsilon(t)/dt$
where $C_1$, $C_2$ and $C_3$ are constants, FL(t) is the air flow, "t" is the time, and "$\varepsilon$" stands for error.

40. An Activity Environment Generator (AEG) apparatus for the exercise of specific body areas of a user and, in particular, for wellness, rehabilitation, physiotherapy, injury prevention, falls prevention and training in general; the AEG apparatus including:
   i. one or more AEG-Master Unit/s (AEG-MU);
   ii. one or more AEG Slave Unit/s (AEG-SU), wherein said AEG-SU and/or said AEG-MU optionally include one or more sensors in order to measure distance and/or position and/or speed between the AEG-MU and the AEG-SU, said one or more sensors being one of the following kinds: distance transducers, distance sensors, tilt sensors, ultrasonic sensors, position sensors, magnetic position switches, proximity sensors, mechanical switches, variable reluctance sensors, or any other equivalent kind of sensor;
   iii. one or more pneumatic actuator/s connected to a compressed air source, said compressed air source being optionally connected to a power source;
   iv. a physical connection between the AEG-MU and the AEG-SU in order to allow the pneumatic actuator/s, which produce/s pressure to act, through said physical connection, on the AEG-MU and the AEG-SU;
   v. a pneumatic actuator controller that controls all operations of the AEG-MU, including a control loop and pull and/or push force between the AEG-MU and AEG-SU, wherein the AEG apparatus is capable of applying force in both directions along an axis of motion, and wherein said AEG apparatus is optionally equipped with lineal and/or rotatory capabilities;
   vi. a pressure transducer which transforms pressure produced by the pneumatic actuator from mechanical force into an electrical signal;
   vii. an electric to pressure signal converter that converts a computed air flow value from the electric signal into an air flow signal;
   viii. software for carrying out a session of the AEG apparatus including changing the pull or push force between the AEG-MU and the AEG-SU based on an error generated by the control loop;

ix. memory for both storing data and for running commands and executing any required process, including those of a software application; and x. a connectivity unit which enables communication between the AEG-MU and other elements including with a communication device, a remote trainer, a cloud, big data in a cloud, and a human machine interface.

41. The apparatus according to claim 40 whereby at least one element of the AEG apparatus is attached to at least one part of the user's body, said part is typically, but not exclusively: a limb, the neck, the head, fingers, toes, knee, elbow, the jaw.

42. The apparatus according to claim 40, wherein at least one AEG element out of the following: the AEG-MU, the AEG-SU, the master electromagnet controller, the force transducer, the memory, the connectivity unit, or the human machine interface, is attached to an external object rather than being attached to the user, and wherein said external object is, typically but not exclusively, one of: a mat, any floor-like surface, a seat, the back of an armchair, an airplane seat, a TV chair, an office chair, a train seat, a wall, a door, any surface, or a domestic or an hospital bed.

43. The apparatus according to claim 40, wherein a number of AEG-MU are attached to an airplane seat and a number of AEG-SU are attached to the user.

44. The apparatus according to claim 40, wherein said apparatus is structured as an exercise mat and comprises:

i. a first set of two or more physical elements, each of said first set of physical elements being optionally provided with one or more AEG-MU;

ii. a second set of two or more physical elements, each of said second set of physical elements being moveable and provided with one or more AEG-MU;

iii. an arrangement that allows the first set of physical elements and the second set of physical elements to be joined together; and iv. a head band to be worn by the user, said head band being equipped with at least one AEG-SU capable of interacting with the AEG-MU on the exercise mat.

45. The apparatus according to claim 40, wherein the AEG apparatus is suitable for exercise of the fingers and of the hand, and the AEG apparatus comprises:

i. an AEG-MU attached to the palm of the hands; and ii. one or more AEG-SU attached to the fingers;

wherein said AEG-MU and said AEG-SU are either physically attached and in interaction.

46. The apparatus according to claim 45, wherein the AEG-MU and the AEG-SU are joined by a frame which is provided and on which frame the AEG-MU or the AEG-SU may be plugged or removed from.

* * * * *

UNITED STATES PATENT AND TRADEMARK OFFICE
CERTIFICATE OF CORRECTION

PATENT NO. : 11,000,736 B2
APPLICATION NO. : 16/756436
DATED : May 11, 2021
INVENTOR(S) : Luzzatto It is certified that error appears in the above-identified patent and that said Letters Patent is hereby corrected as shown below:

In the Claims

Column 14,
Line 59, "monitors or" should read --monitors, or--;
Line 60, "session, is" should read --session is--.

Column 15,
Line 10, "— or" should read --or--;
Line 12, "session, is" should read --session is--;
Line 42, the formula should read --$I(t) = C_1 \times \mathcal{E}(t) + C_2 \times \int \mathcal{E}(t)dt + C_3 \times d\mathcal{E}(t)/dt$--;
Line 48, "session, is" should read --session is--.

Column 16,
Line 27, the formula should read --$FL(t) = C_1 \times \mathcal{E}(t) + C_2 \times \int \mathcal{E}(t)dt + C_3 \times d\mathcal{E}(t)/dt$--.

Signed and Sealed this
Fourteenth Day of June, 2022

Katherine Kelly Vidal
*Director of the United States Patent and Trademark Office*